US007923583B2

(12) United States Patent
Hoshino et al.

(10) Patent No.: US 7,923,583 B2
(45) Date of Patent: Apr. 12, 2011

(54) METHOD FOR PRODUCING CYCLOALKANOL AND/OR CYCLOALKANONE

(75) Inventors: Masahiro Hoshino, Niihama (JP); Nobufumi Watanabe, Niihama (JP); Keisuke Sugita, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/392,122

(22) Filed: Feb. 25, 2009

(65) Prior Publication Data

US 2009/0227814 A1 Sep. 10, 2009

(30) Foreign Application Priority Data

Feb. 29, 2008 (JP) ................................ 2008-049509

(51) Int. Cl.
*C07C 45/33* (2006.01)
*C07C 35/08* (2006.01)
(52) U.S. Cl. ......... 568/357; 568/360; 568/822; 568/836
(58) Field of Classification Search .................. 568/357, 568/822
See application file for complete search history.

(56) References Cited

U.S. PATENT DOCUMENTS

| 5,098,684 | A * | 3/1992 | Kresge et al. ................. 423/718 |
| 6,806,390 | B1 | 10/2004 | Herron et al. |
| 7,541,500 | B2 * | 6/2009 | Hoshino ....................... 568/360 |
| 2008/0076946 | A1 | 3/2008 | Hoshino et al. |
| 2008/0228007 | A1 | 9/2008 | Hoshino et al. |

FOREIGN PATENT DOCUMENTS

WO 00/03963 A1 1/2000

OTHER PUBLICATIONS

G. Lu et al., "Gold nanoparticles in mesoporous materials showing catalytic selective oxidation cyclohexane using oxygen", Applied Catalysis A: General 280, (2005), pp. 175-180.
S. Liu, et al. "Liquid-Phase Oxidation of Cyclohexane Using Co-P-MCM-41 Catalyst", Korean J. Chem. Eng., 15 (5), 1998, pp. 510-515.
A. Sayari et al., "Application of Pore-Expanded Mesoporous Silica. 1. Removal of Heavy Metal Cations and Organic Pollutants from Wastewater", Chem. Mater. (2005), 17, pp. 212-216.
P. Karandikar et al., "Liquid phase oxidation of alkanes using Cu/Co-perchlorophthalocyanine immobilized MCM-41 under mild reaction conditions," Applied Catalysis A: General, vol. 297, 2006, pp. 220-230.
P. Karandikar et al., "Cu2+-perchlorophthalocyanine immobilized MCM-41: catalyst for oxidation of alkenes", Applied Catalysis A: General, vol. 257, 2004, pp. 133-143.

* cited by examiner

*Primary Examiner* — Sikarl A Witherspoon
(74) *Attorney, Agent, or Firm* — Sughrue Mion, PLLC

(57) ABSTRACT

An object of the present invention is to provide a method capable of producing a cycloalkanol and/or a cycloalkanone with a favorable selectivity coefficient by oxidizing a cycloalkane with a favorable conversion ratio.
Disclosed is a method for producing a cycloalkanol and/or a cycloalkanone, which comprises oxidizing a cycloalkane with oxygen in the presence of a mesoporous silica which contains at least one transition metal and has been also subjected to contact treatment with an amine and/or ammonia. Preferably, a crystal obtained by mixing a compound containing the metal, a silicon compound, a structure-directing agent and water is subjected to contact treatment with an amine and/or ammonia and then fired to obtain a mesoporous silica, and a cycloalkane is oxidized with oxygen in the presence of the mesoporous silica.

6 Claims, 1 Drawing Sheet

METHOD FOR PRODUCING CYCLOALKANOL AND/OR CYCLOALKANONE

BACKGROUND OF THE INVENTION

1. Field of the Invention

The present patent application claims priority under the Paris Convention based on Japanese Patent Application No. 2008-049509 (filed on Feb. 29, 2008), and the entire content of the aforementioned application is herein incorporated by reference.

The present invention relates to a method for producing a cycloalkanol and/or a cycloalkanone by oxidizing a cycloalkane with oxygen.

2. Description of the Related Art

In a method for producing a cycloalkanol and/or a cycloalkanone by oxidizing a cycloalkane with oxygen, a method of performing the oxidation reaction using a mesoporous silica containing a certain kind of a metal element as a catalyst has been studied. For example, there are known a method using a mesoporous silica containing gold (International Publication No. WO 00/03963 pamphlet), a method using a mesoporous silica containing cobalt (Applied Catalysis, Netherlands, 2005, Vol. 280, pp.175-180, and a method using a mesoporous silica containing chromium or vanadium (Korean Journal of Chemical Engineering, Republic of Korea, 1998, Vol. 15, pp. 510-515).

SUMMARY OF THE INVENTION

The above-mentioned conventional methods include unsatisfactory points in view of activity and selectivity of a catalyst, namely, a conversion ratio of a cycloalkane and a selectivity coefficient of a cycloalkanol and/or a cycloalkanone. Thus, an object of the present invention is to provide a method capable of producing a cycloalkanol and/or a cycloalkanone with a favorable selectivity coefficient by oxidizing a cycloalkane with a favorable conversion ratio.

The present inventors have intensively studied and found that the above object can be achieved by performing the above oxidation reaction in the presence of a mesoporous silica which contains at least one kind of a transition metal and has been also subjected to contact treatment with an amine and/or ammonia. Thus, the present invention has been completed.

The present invention provides a method for producing a cycloalkanol and/or a cycloalkanone, which comprises oxidizing a cycloalkane with oxygen in the presence of a mesoporous silica which contains at least one transition metal and has been also subjected to contact treatment with an amine and/or ammonia.

According to the present invention, a cycloalkanol and/or a cycloalkanone can be produced with a favorable selectivity coefficient by oxidizing a cycloalkane with a favorable conversion ratio.

DETAILED DESCRIPTION OF THE INVENTION

Figure 1:
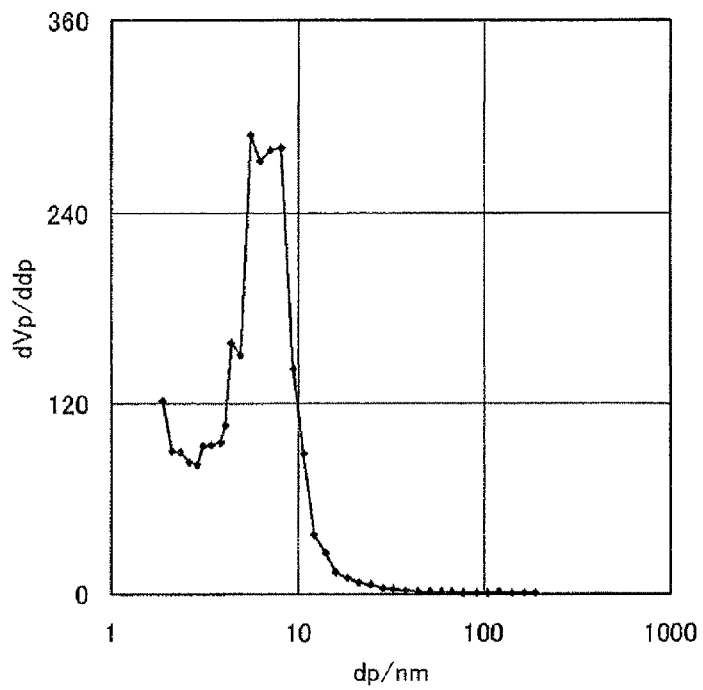
FIG. 1 is a graph showing pore distribution of a mesoporous silica obtained in Example 1(C).

The present invention will now be described in detail. In the present invention, corresponding cycloalkanol and/or cycloalkanone are produced by oxidizing a cycloalkane used as a material with oxygen (molecular oxygen) in the presence of a predetermined mesoporous silica.

Examples of the cycloalkane as the material include monocyclic cycloalkanes having no substituent on the ring, such as cyclopropane, cyclobutane, cyclopentane, cyclohexane, cycloheptane, cyclooctane, cyclodecane, and cyclooctadecane; polycyclic cycloalkanes such as decalin and adamantane; and cycloalkanes having a substituent on the ring, such as methylcyclopentane and methylcyclohexane, and two or more kinds of them can be used, if necessary.

An oxygen-containing gas is usually used as an oxygen source. This oxygen-containing gas may be, for example, an air, pure oxygen, or an air or pure oxygen diluted with an inert gas such as nitrogen, argon or helium. Oxygen enriched air obtained by adding pure oxygen to an air can also be used.

In the present invention, the above oxidation reaction is performed in the presence of a mesoporous silica which contains at least one kind of a transition metal and has been also subjected to contact treatment with an amine and/or ammonia. When such a mesoporous silica is used, a cycloalkanol and/or a cycloalkanone can be produced with a favorable selectivity coefficient by oxidizing a cycloalkane with a favorable conversion ratio.

Examples of the metal to be contained in the mesoporous silica include transition metals and are preferably vanadium, chromium, manganese, iron, cobalt, ruthenium and palladium. Of these metals, cobalt is preferable. If necessary, two or more kinds of these metals may be used. The content of the metal is usually from 0.01 to 20%, preferably from 0.05 to 10%, and still more preferably from 0.1 to 5%, in terms of a weight ratio of the metal to the mesoporous silica.

The mesoporous silica in the present invention has a so-called mesoporous structure containing pores which usually have nearly uniform size of 2 to 50 nm, and the surface area is usually from about 600 to 1,500 $m^2/g$. The metal may be incorporated into a silica framework composing the mesoporous structure, or may be incorporated into the pores, or may be supported on the surface of the silica framework. Examples of the mesoporous silica include a MCM-41 type mesoporous silica, a MCM-48 type mesoporous silica, a FSM-16 type mesoporous silica, a SBA-15 type mesoporous silica and a HMS type mesoporous silica, of which a MCM-41 type mesoporous silica is preferable. The presence or absence of the mesoporous structure can be confirmed by the presence or absence of a peak $2\theta$ of 0.2 to 4.0° in the measurement of XRD (X-ray diffraction).

The method for preparing the mesoporous silica in the present invention will now be described. The mesoporous silica to be used in the present invention may be prepared by obtaining a crystal containing the transition metal using also a compound containing the transition metal as a raw material when a known production method of a silica having a mesoporous structure is conducted, and subjecting the resultant crystal to contact treatment with an amine and/or ammonia; by contacting a silica having a mesoporous structure obtained by a known method with a compound containing the transition metal and then contacting the resultant with an amine and/or ammonia; or by contacting a silica having a mesoporous structure obtained by a known method with an amine and/or ammonia and then contacting the resultant with a compound containing the transition metal. In particular, for example, a silicon compound, a structure-directing agent and water are mixed and the resultant crystal (silica having a mesoporous structure) is subjected to contact treatment with an amine and/or ammonia and then fired to prepare a desired mesoporous silica. A silica having a mesoporous structure can be prepared by known methods described in Korean Journal of Chemical Engineering, Republic of Korea, 1998, Vol. 15, pp. 510-515, and Nature, U.S.A., 1992, Vol. 359, pp. 710-712. For example, the silica can be prepared by mixing a silicon compound such as tetraalkoxysilane, a structure-directing agent such as a quaternary ammonium salt, and water, and optionally heat-treating the mixture to obtain a crystal, followed by filtration and further drying. In the present invention, in order to allow a mesoporous silica to contain a transition metal, a compound containing a transition metal (hereinafter may be referred to as a metal compound) may be mixed with the silicon compound, the structure-directing agent and water, or may be supported on the crystal, or may be supported on a crystal obtained by contact treatment with an amine and/or ammonia. It is particularly preferable to mix the metal compound with the silicon compound, the structure-directing agent and water.

Examples of the silicon compound include tetraalkoxysilanes such as tetramethoxysilane, tetraethoxysilane, tetrapropoxysilane and tetrabutoxysilane, and two or more kinds of them can be used, if necessary.

Examples of structure-directing agent include alkyltrimethylammonium bromides having 19 to 21 carbon atoms, such as hexadecyltrimethylammoniun bromide, heptadecyltrimethylammoniun bromide and octadecyltrimethylammoniun bromide; alkyltrimethylammonium chlorides having 19 to 21 carbon atoms, such as hexadecyltrimethylammoniun chloride, heptadecyltrimethylammoniun chloride and octadecyltrimethylammoniun chloride; and alkyltrimethylammonium hydroxides having 19 to 21 carbon atoms, such as hexadecyltrimethylammoniun hydroxide, heptadecyltrimethylammoniun hydroxide and octadecyltrimethylammoniun hydroxide, and two or more kinds of them can be used, if necessary. Of these structure-directing agents, alkyltrimethylammonium bromides are preferable and hexadecyltrimethylammonium bromide is more preferable.

When the silicon compound, the structure-directing agent and water are mixed, ammonia and/or an alcohol are preferably mixed together with them since a mesoporous silica having a small particle diameter can be obtained. Ammonia may be liquid or gaseous ammonia. Also, ammonia water may be used. Such an alcohol can be an aliphatic alcohol having about 1 to 6 carbon atoms and specific examples thereof include methanol, ethanol, propanol, butanol, pentanol and hexanol. If necessary, two or more kinds of them can also be used. Of these alcohols, ethanol is preferable.

The amount of the structure-directing agent used is usually from 0.1 to 1.0 mol, and preferably from 0.2 to 0.5 mol, based on 1 mol of the silicon compound. The amount of water used is usually from 5 to 30 parts by weight, and preferably from 10 to 15 parts by weight, based on 1 part by weight of the tetraalkoxysilane.

The temperature of mixing of the silicon compound, the structure-directing agent and water is usually from 20 to 200° C., and preferably from 20 to 150° C. The mixing time is usually from 0.1 to 400 hours, and preferably from 1 to 200 hours.

Thus, a silica crystal having a mesoporous structure can be obtained. In the present invention, this crystal is fired after subjecting to contact treatment with an amine and/or ammonia. A mesoporous silica containing pores having a larger size can be prepared by firing after performing the contact treatment. The contact treatment is preferably applied to a crystal obtained by filtering a suspension, which is obtained by mixing the silicon compound, the structure-directing agent and water, followed by drying.

The amine as used herein can be usually a primary, secondary or tertiary amine bonded with an alkyl group having about 1 to 20 carbon atoms. Of these amines, a tertiary amine is preferable, and a dimethylalkylamine such as dimethyldecylamine and a triakylamine are more preferable.

The amine and/or ammonia may be used for the contact treatment as they are, or may be used in the form of an aqueous solution. The amount of the amine and/or ammonia used is usually from 1 to 1,500 parts by weight, preferably from 5 to 300 parts by weight, and more preferably from 10 to 150 parts by weight, based on 100 parts by weight of the crystal before subjecting to the contact treatment. The temperature of the contact treatment is usually from 0 to 300° C., and preferably from 30 to 250° C. The time of the contact treatment is usually from 0.1 to 2,000 hours, and preferably from 1 to 200 hours.

In the present invention, filtration, drying and firing are usually performed after performing the contact treatment. Drying is usually performed under a nitrogen atmosphere, and the drying temperature is from about 40 to 120° C. and the drying time is from about 2 to 24 hours. Firing is usually performed under a nitrogen atmosphere. The firing temperature is from 450 to 650° C., and preferably from 500 to 600° C., and the firing time is usually from 4 to 12 hours, and preferably from 6 to 10 hours.

The mesoporous silica of the present invention contains at least one kind of a transition metal and, as described above, in order to allow the mesoporous silica to contain the metal, the metal compound may be mixed with the silicon compound, the structure-directing agent and water, or may be supported on a crystal obtained by mixing the silicon compound, the structure-directing agent and water, or may be supported on a crystal obtained by contact treatment of the amine and/or ammonia. Specific examples of the method include (1) a method in which the metal compound such as halide, nitrate, sulfate, carboxylate, oxo acid salt or hydroxide of metal is added when the silicon compound, the structure-directing agent and water are mixed, (2) a method in which a crystal obtained by mixing the silicon compound, the structure-directing agent and water is impregnated with a solution of the metal compound, and (3) a method in which a crystal obtained by mixing the silicon compound, the structure-directing agent and water is immersed in a solution of the metal compound thereby adsorbing the metal compound to the crystal, or metal cations of the metal compound are exchanged by cations of the crystal. The amount of the metal compound used is appropriately adjusted so as to adjust to the above content of the metal.

It is possible to use, as the material of the transition metal, vanadium compounds such as vanadium bromide, vanadium chloride, vanadium fluoride and vanadium naphthate; chromium compounds such as chromium chloride, chromium nitrate, chromium sulfate, chromium acetate and chromium naphthate; manganese compounds such as manganese bromide, manganese chloride, manganese fluoride, manganese nitrate, manganese ammonium sulfate, manganese sulfate, manganese acetate and manganese naphthate; iron compounds such as iron bromide, iron chloride, iron fluoride, iron nitrate, iron sulfate, iron acetate and iron naphthate; cobalt compounds such as cobalt bromide, cobalt chloride, cobalt fluoride, cobalt nitrate, cobalt sulfate, cobalt acetate and cobalt naphthate; ruthenium compounds such as ruthenium bromide and ruthenium chloride; and palladium compounds such as palladium bromide, palladium chloride, palladium nitrate, palladium sulfate and palladium hydroxide. Of these compounds, cobalt compounds are preferable.

In the present invention, it is more effective to performing contact treatment with an organosilicon compounds after firing. The organosilicon compound is preferably reacted with the mesoporous silica to bond on the surface, and can be typically represented by the following formula (1):

$$Si(R^1)_x(R^2)_{4-x} \tag{1}$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

Examples of the alkoxy group represented by $R^1$ and $R^2$ include a methoxy group, an ethoxy group, a propoxy group and a butoxy group, and examples of the alkyl group represented by $R^2$ include a methyl group, an ethyl group, a propyl group and a butyl group. Examples of the aryl group represented by $R^2$ include a phenyl group, a naphthyl group and a tolyl group, and examples of the aralkyl group represented by $R^2$ include a benzyl group and a phenetyl group.

As the organosilicon compound represented by the formula (1), a trialkoxyalkylsilane and a tetraalkoxysilane are more preferably used.

The method of subjecting to contact treatment with an organosilicon compound includes, for example, a method in which a crystal (mesoporous silica) after firing is immersed in a liquid containing an organosilicon compound, and a method in which a gas containing an organosilicon compound is brought into contact with a crystal (mesoporous silica) after firing.

The amount of the organosilicon compound used is usually from 1 to 10,000 parts by weight, preferably from 5 to 2,000 parts by weight, and more preferably from 10 to 1,500 parts by weight, based on 100 parts by weight of the silica before subjecting to the contact treatment.

The temperature of the contact treatment is usually from 0 to 300° C., and preferably from 30 to 250° C. The time of the contact treatment is usually from 0.1 to 50 hours, and preferably from 1 to 20 hours.

Thus, the desired mesoporous silica can be obtained. Then, a cycloalkane is oxidized with oxygen in the presence of the mesoporous silica. The amount of the mesoporous silica used is usually from 0.0001 to 50 parts by weight, and preferably from 0.001 to 10 parts by weight, based on 100 parts by weight of the cycloalkane.

The temperature of the oxidation reaction is usually from 0 to 200° C., and preferably from 50 to 170° C., and the reaction pressure is usually from 0.01 to 10 MPa, and preferably from 0.1 to 2 MPa. A reaction solvent can be optionally used and, for example, nitrile solvents such as acetonitrile or benzonitrile, and carboxylic acid solvents such as acetic acid or propionic acid can be used.

A post-treatment after the oxidation reaction is not specifically limited and examples thereof include a method in which a catalyst is separated by filtering the reaction mixture, followed by washing with water and further distillation. When cycloalkyl hydroperoxide corresponding to the cycloalkane as the material is contained in the reaction mixture, it can be converted into the objective cycloalkanol and cycloalkanone by an alkali treatment or a reduction treatment.

EXAMPLES

Examples of the present invention will now be described, but are not limited thereto. Cyclohexane, cyclohexanone, cyclohexanol and cyclohexyl hydroperoxide in the reaction solution were analyzed by gas chromatography, and the conversion ratio of cyclohexane as well as each selectivity coefficient of cyclohexanone, cyclohexanol and cyclohexyl hydroperoxide were calculated from the analysis results.

In Examples, pore distribution of a silica (crystal) having a mesoporous structure was determined by BJH analysis of an adsorption isotherm of a volumetric method at a liquid nitrogen temperature (77 K). The procedure for the measurement is as follows.

A glass test tube (volume: 4 ml, inner diameter: 6 mm) was set in BELPREP-vacII manufactured by BEL Japan, Inc. and evacuated and, after tare measuring, about 0.05 g of a powder sample was filled in the test tube. After evacuating the test tube was evacuated again at 150° C. for 3 hours using BELPREP-vacII, the test tube was weighed again and a tare weight is subtracted to obtain a true amount of the powder sample. Next, the test tube subjected to a vacuum pretreatment was set in BELPREP-mini manufactured by BEL Japan, Inc. and a volume (dead volume) peculiar to each test tube was measured and, after measuring a saturated vapor pressure of nitrogen, an adsorption equilibrium pressure was measured. These operations were repeated until a relative pressure as a ratio of the adsorption equilibrium pressure to an initial pressure reaches 0.99 to obtain an adsorption isotherm. Pore distribution was derived by calculating a pore diameter and a pore volume from the Barrett-Joyner-Halenda (BJH) theory utilizing capillary condensation of a nitrogen gas under assumption of a cylindrical pore and then plotting a change in an amount of the pore volume to the pore diameter.

Example 1

(A) Preparation of Silica having Mesoporous Structure

Hexadecyltrimethylammonium bromide (17.59 g) (manufactured by Wako Pure Chemical Industries, Ltd.), 327.11 g of water, 106.94 g of ethanol (manufactured by Wako Pure Chemical Industries, Ltd.), 33.76 g of tetraethoxysilane (ethyl orthosilicate, manufactured by Wako Pure Chemical Industries, Ltd.), 119.34 g of 25% ammonia water (manufactured by Wako Pure Chemical Industries, Ltd.) and 0.0418 g of cobalt(II) acetate tetrahydrate (manufactured by Wako Pure Chemical Industries, Ltd.) were charged in a 1 liter beaker, stirred at room temperature for 2 hours and then filtered. The residue was washed with water and then dried at 100° C. for 12 hours to obtain a crystal A.

(B) Contact Treatment with Amine, and Firing

The crystal A (4.27 g) obtained in Example 1(A), 7.91 g of dimethyldecylamine (manufactured by Tokyo Kasei Kogyo Co., Ltd.) and 87.82 g of ultrapure water were charged in a 300 ml beaker and then stirred at 25° C. for 50 minutes. After transferring to a 200 ml autoclave and standing at 120° C. for 4 days, the resultant mixture was filtered. The residue was washed with water and then dried at 100° C. for 12 hours. The residue was fired under an air flow at 550° C. for 7 hours to obtain a crystal B. With respect to the crystal B, pore distribution was determined by the method described above. As a result, a peak attributed to the presence of pores having a size of 6 to 8 nm was observed. The pore distribution is shown in FIG. 1. The ordinate of FIG. 1 denotes a change in a pore volume (dVp/ddp), whereas, the abscissa denotes a pore diameter (dp [nm]).

(C) Contact Treatment with Trimethoxypropylsilane

The crystal B (1.0 g) obtained in Example 1(B) and 10.0 g of trimethoxypropylsilane (manufactured by Tokyo Kasei Kogyo Co., Ltd.) were charged in a flask and then stirred under a nitrogen atmosphere at 90° C. for 7.5 hours. The resultant mixture was cooled to room temperature and ethanol was added, followed by stirring and further filtration. The residue was washed with ethanol, dried under 0.1 Torr (13 Pa) at 40° C. for one hour and then dried at 100° C. to obtain a mesoporous silica X.

(D) Evaluation of Reaction

In a 1 liter autoclave, 278 g (3.3 mol) of cyclohexane and 1.0 g of the mesoporous silica X obtained in Example 1(C) were charged. After increasing the pressure in the system to 0.93 MPa at room temperature using nitrogen and heating to 140° C., the reaction was carried out under the flow of a gas having an oxygen concentration of 15% by volume for 7 hours.

Three hours after the beginning of the reaction, the conversion ratio of cyclohexane was 6.2%, the selectivity coefficient of cyclohexanone was 30.6%, the selectivity coefficient of cyclohexanol was 44.3%, and the selectivity coefficient of cyclohexyl hydroperoxide was 8.7% (total selectivity coefficient: 83.6%). Five hours after the beginning of the reaction, the conversion ratio of cyclohexane was 8.5%, the selectivity coefficient of cyclohexanone was 34.3%, the selectivity coefficient of cyclohexanol was 40.1%, and the selectivity coefficient of cyclohexyl hydroperoxide was 7.6% (total selectivity coefficient: 82.0%). Seven hours after the beginning of the reaction (upon completion), the conversion ratio of cyclohexane was 10.7%, the selectivity coefficient of cyclohexanone was 37.4%, the selectivity coefficient of cyclohexanol was 36.7%, and the selectivity coefficient of cyclohexyl hydroperoxide was 6.2% (total selectivity coefficient: 80.3%).

Comparative Example 1

(E) Preparation of Silica having Mesoporous Structure

Figure 2:
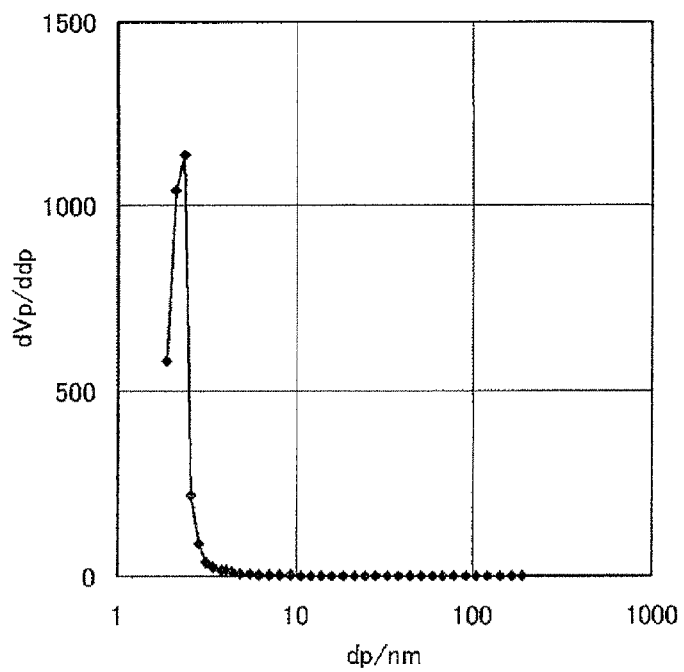
FIG. 2 is a graph showing pore distribution of a mesoporous silica obtained in Comparative Example 1(F).

Hexadecyltrimethylammonium bromide (17.59 g) manufactured by Wako Pure Chemical Industries, Ltd.), 327.11 g of water, 106.94 g of ethanol (manufactured by Wako Pure Chemical Industries, Ltd.), 33.76 g of tetraethoxysilane (ethyl orthosilicate, manufactured by Wako Pure Chemical Industries, Ltd.), 119.34 g of 25% ammonia water (manufactured by Wako Pure Chemical Industries, Ltd.) and 0.0418 g of cobalt(II) acetate tetrahydrate (manufactured by Wako Pure Chemical Industries, Ltd.) were charged in a 1 liter beaker, stirred at room temperature for 2 hours and then filtered. The residue was washed with water, dried at 100° C. for 12 hours and then fired under an air flow at 550° C. for 7 hours to obtain a crystal E. With respect to the crystal E, pore distribution was determined by the method described above. As a result, a peak attributed to the presence of pores having a size of 2 to 3 nm was observed. The pore distribution is shown in FIG. 2. The ordinate of FIG. 2 denotes a change in a pore volume (dVp/ddp), whereas, the abscissa denotes a pore diameter (dp [nm]).

(F) Contact Treatment with Trimethoxypropylsilane

The crystal (1.0 g) obtained in Comparative Example 1(E) and 10.0 g of trimethoxypropylsilane (manufactured by Tokyo Kasei Kogyo Co., Ltd.) were charged in a flask and then stirred under a nitrogen atmosphere at 90° C. for 7.5 hours. The resultant mixture was cooled to room temperature and ethanol was added, followed by stirring and further filtration. The residue was washed with ethanol, dried under 0.1 Torr (13 Pa) at 40° C. for one hour and then dried at 100° C. to obtain a mesoporous silica Y.

(G) Evaluation of Reaction

The same operation was performed, except that the mesoporous silica Y obtained in Comparative Example 1(F) was used in place of the mesoporous silica X obtained in Example 1(C).

Three hours after the beginning of the reaction, the conversion ratio of cyclohexane was 6.0%, the selectivity coefficient of cyclohexanone was 31.8%, the selectivity coefficient of cyclohexanol was 41.6%, and the selectivity coefficient of cyclohexyl hydroperoxide was 8.7% (total selectivity coefficient: 82.1%). Five hours after the beginning of the reaction, the conversion ratio of cyclohexane was 7.6%, the selectivity coefficient of cyclohexanone was 35.1%, the selectivity coefficient of cyclohexanol was 40.9%, and the selectivity coefficient of cyclohexyl hydroperoxide was 4.1% (total selectivity coefficient: 80.1%). Seven hours after the beginning of the reaction (upon completion), the conversion ratio of cyclohexane was 10.0%, the selectivity coefficient of cyclohexanone was 37.2%, the selectivity coefficient of cyclohexanol was 36.3%, and the selectivity coefficient of cyclohexyl hydroperoxide was 4.2% (total selectivity coefficient: 77.7%).

The major embodiments and the preferred embodiments of the present invention are listed below.

[1] A method for producing a cycloalkanol and/or a cycloalkanone, which comprises oxidizing a cycloalkane with oxygen in the presence of a mesoporous silica which contains at least one transition metal and has been also subjected to contact treatment with an amine and/or ammonia.

[2] The method according to [1], wherein the mesoporous silica is prepared by mixing a compound containing the metal, a silicon compound, a structure-directing agent and water to obtain a crystal, subjecting the crystal to contact treatment with an amine and/or ammonia, and then firing the resultant.

[3] The method according to [2], wherein the mesoporous silica is prepared by, after firing, subjecting the fired resultant to contact treatment with an organosilicon compound represented by the formula (1):

$$Si(R^1)_x(R^2)_{4-x} \qquad (1)$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

[4] The method according to any one of [1] to [3], wherein the mesoporous silica is MCM-41 type mesoporous silica.

[5] The method according to any one of [1] to [4], wherein the metal is at least one metal selected from the group consisting of vanadium, chromium, manganese, iron, cobalt, ruthenium and palladium.

[6] The method according to any one of [1] to [4], wherein the metal is cobalt.

[7] The method according to any one of [1] to [6], wherein the cycloalkane is cyclohexane.

What is claimed is:

1. A method for producing a cycloalkanol and/or a cycloalkanone, which comprises oxidizing a cycloalkane with molecular oxygen in the presence of a mesoporous silica which contains at least one transition metal, wherein the mesoporous silica is prepared by mixing a compound containing the transition metal, a silicon compound, a structure-directing agent and water to obtain a crystal, subjecting the crystal to contact treatment with an amine and/or ammonia, and then firing the resultant, and subjecting the fired resultant to contact treatment with an organosilicon compound represented by the formula (1):

$$Si(R^1)_x(R^2)_{4-x} \qquad (1)$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

2. The method according to claim 1, wherein the mesoporous silica is MCM-41 type mesoporous silica.

3. The method according to claim 1, wherein the metal is at least one metal selected from the group consisting of vanadium, chromium, manganese, iron, cobalt, ruthenium and palladium.

4. The method according to claim 1, wherein the metal is cobalt.

5. The method according to claim 1, wherein the cycloalkane is cyclohexane.

6. The method according to claim 1, wherein the amine is a primary, secondary or tertiary amine bonded with an alkyl group having 1 to 20 carbon atoms.

\* \* \* \* \*